US009671334B2

(12) United States Patent
Lear et al.

(10) Patent No.: US 9,671,334 B2
(45) Date of Patent: Jun. 6, 2017

(54) MULTI-ANALYTE OPTICAL SENSOR

(71) Applicant: Colorado State University Research Foundation, Fort Collins, CO (US)

(72) Inventors: Kevin L. Lear, Fort Collins, CO (US); Timothy A. Erickson, Beaverton, OR (US)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 81 days.

(21) Appl. No.: 14/437,039

(22) PCT Filed: Oct. 25, 2013

(86) PCT No.: PCT/US2013/066926
§ 371 (c)(1),
(2) Date: Apr. 20, 2015

(87) PCT Pub. No.: WO2014/066826
PCT Pub. Date: May 1, 2014

(65) Prior Publication Data
US 2015/0268162 A1    Sep. 24, 2015

Related U.S. Application Data

(60) Provisional application No. 61/718,594, filed on Oct. 25, 2012.

(51) Int. Cl.
*H01J 40/14* (2006.01)
*G02B 6/00* (2006.01)
(Continued)

(52) U.S. Cl.
CPC ..... *G01N 21/4133* (2013.01); *G01N 21/7703* (2013.01); *H01L 31/105* (2013.01);
(Continued)

(58) Field of Classification Search
CPC ................................................. G01N 21/7703
(Continued)

(56) References Cited

U.S. PATENT DOCUMENTS

| 4,125,316 A | 11/1978 | Stotts et al. |
| 4,436,995 A | 3/1984 | Whitten |

(Continued)

FOREIGN PATENT DOCUMENTS

| WO | WO 00/62105 | 10/2000 |
| WO | WO 2009/103339 | 8/2009 |

(Continued)

OTHER PUBLICATIONS

PCT/US2013/066962 International Search Report & Written Opinion mailed Jan. 16, 2014; 13 pages.

(Continued)

*Primary Examiner* — Thanh Luu
(74) *Attorney, Agent, or Firm* — Lathrop & Gage LLP

(57) ABSTRACT

An analyte-detection system has an optical waveguide with first and second cladding layers adjacent a core; a light source coupled to provide light to the waveguide; a photodetector such as a metal-semiconductor-metal, vertical PIN, or horizontal PIN photodetectors, the photodetector having an absorber configured to detect light escaping from the waveguide through the first cladding layer; multiple, separate, photocurrent collectors, where each photocurrent collector collects current from a separate portion of the photodetector absorber; and at least one current-sensing amplifier for receiving photocurrent. The photodetector absorber is an undivided absorber region for multiple photocurrent collectors. Either separate amplifiers are provided for each of the multiple photocurrent collection lines, or multiplexing logic (Continued)

couples selected photocurrent collectors to amplifiers, while coupling unselected photocurrent collectors to a bias generator.

17 Claims, 7 Drawing Sheets

(51) Int. Cl.
 *G01N 21/41* (2006.01)
 *G01N 21/77* (2006.01)
 *H01L 31/105* (2006.01)
 *H01L 31/108* (2006.01)

(52) U.S. Cl.
 CPC .. *H01L 31/1085* (2013.01); *G01N 2021/7793* (2013.01); *G01N 2201/0833* (2013.01)

(58) Field of Classification Search
 USPC .......................................... 250/214 R; 385/12
 See application file for complete search history.

(56) References Cited

U.S. PATENT DOCUMENTS

| | | |
|---|---|---|
| 4,472,628 A | 9/1984 | Whitten |
| 4,751,710 A | 6/1988 | Yamaguchi et al. |
| 4,794,249 A | 12/1988 | Beckmann et al. |
| 5,025,147 A | 6/1991 | Durig et al. |
| 5,218,198 A | 6/1993 | Bristow et al. |
| 5,317,147 A | 5/1994 | Dandliker et al. |
| 5,347,601 A | 9/1994 | Ade et al. |
| 5,391,869 A | 2/1995 | Ade et al. |
| 5,712,864 A | 1/1998 | Goldstein et al. |
| 6,076,959 A | 6/2000 | Nagasawa |
| 6,437,345 B1 | 8/2002 | Bruno-Raimondi et al. |
| 6,801,677 B1 | 10/2004 | Grace et al. |
| 6,829,073 B1 | 12/2004 | Krol et al. |
| 6,965,709 B1 | 11/2005 | Weiss |
| 7,149,425 B2 | 12/2006 | Gripp et al. |
| 7,385,460 B1 | 6/2008 | Wang et al. |
| 7,657,129 B2 | 2/2010 | Karras |
| 7,831,146 B2 | 11/2010 | Mazed |
| 7,995,877 B1 | 8/2011 | Skogen et al. |
| 8,014,639 B1 | 9/2011 | Skogen et al. |
| 8,288,157 B2 | 10/2012 | Duer |
| 8,330,952 B2 | 12/2012 | Wu et al. |
| 8,349,605 B1 | 1/2013 | Lear et al. |
| 8,463,084 B2 | 6/2013 | Kurtz et al. |
| 2006/0023992 A1 | 2/2006 | Kish et al. |
| 2009/0111207 A1* | 4/2009 | Choumane ......... G01N 21/6454 438/70 |
| 2010/0065726 A1 | 3/2010 | Zhong et al. |

FOREIGN PATENT DOCUMENTS

| | | |
|---|---|---|
| WO | WO 2009/107041 | 9/2009 |
| WO | WO 2011/157767 | 12/2011 |

OTHER PUBLICATIONS

Supplementary European Search Report in European Patent Application No. 13848232.8 mailed May 2, 2016, 6 pp.

\* cited by examiner

Lateral MSM detector

Lateral PIN

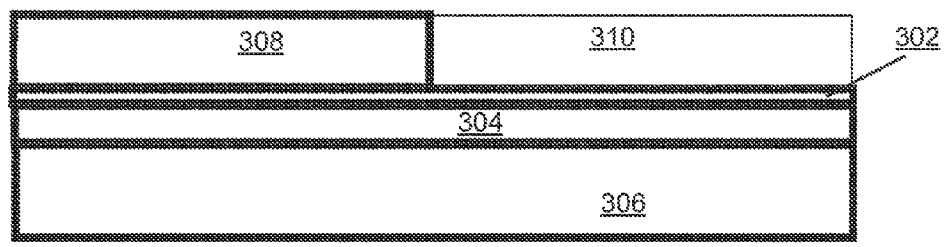
Fig. 5
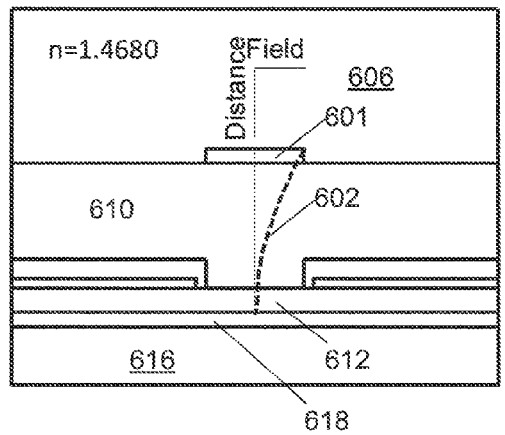 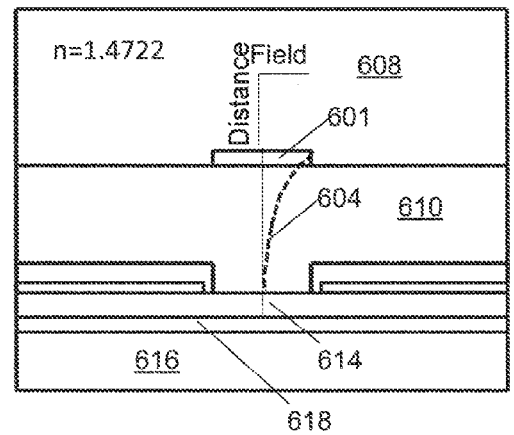
Fig. 6A                                Fig. 6B

MULTI-ANALYTE OPTICAL SENSOR

RELATED APPLICATIONS

The present application claims benefit of priority to U.S. Provisional Patent Application 61/718,594 filed 25 Oct. 2012.

The present document involves sensors that have some features in common with those described in U.S. Pat. No. 8,349,605, but does not claim priority from that patent. The entire disclosures of U.S. Pat. No. 8,349,605 and the above-cited provisional application 61/718,594 are incorporated herein by reference.

FIELD

The present document relates to the fields of refractometers and biosensors.

BACKGROUND

A typical optical waveguide (WG) has a core layer having a high refractive index, surrounded by cladding layers of lower refractive index. The refractive index boundary acts to guide photons reaching the boundary between core and cladding back into the core.

Electromagnetic waves propagating in optical waveguides create evanescent electric and magnetic fields in lower refractive index cladding regions adjacent to the higher refractive index waveguide core. A propagation constant along the axis of the waveguide core and field distributions transverse to the waveguide core depend on the value of the refractive index in the cladding regions. Refractive index sensors have a waveguide core in close proximity to a sample region that essentially forms a part of cladding. Changes in the refractive index within the sample region that overlap field distributions alter the electromagnetic mode profiles and propagation constants of guided waves. Changes in concentration of analyte molecules close enough to the core can change the average refractive index near the core if they have a different refractive index from the host media or solvent that they displace in or near the cladding. The altered refractive index may change propagation in the core, or alter amount of light escaping from the waveguide. Optical waveguides with particular coatings can sense the presence or concentration of certain molecules near the waveguide core.

Previously described are optical waveguides for sensing refractive index and conditions that alter refractive index within the evanescent fields near the waveguide core. Evanescent field optical waveguide sensor devices include Mach-Zehnder interferometers and ring resonators. Similar principles apply to waveguide grating devices and surface plasmon sensors which also provide a sensing mechanism within evanescent fields. Changes in the guided electromagnetic wave's propagation constant may be sensed via changes in the phase of the wave at some point where the light is mixed with a reference beam, as with an interferometer. Alternatively, a change in the propagation constant may alter the resonant wavelength of an optical waveguide resonator. Changes in the propagation constant may also be manifested in the angle of diffraction from a waveguide grating for a fixed wavelength or the angle of light coupled to a surface plasmon.

Recently, the local evanescent array coupled (LEAC) sensor has been developed. LEAC sensors make use of altered refractive index to change the amount of light escaping from the waveguide into a photodetector. LEAC sensors sense changes of refractive index in an upper cladding, or in a fluid that acts as an upper cladding, by altering evanescent coupling of a guided optical wave in a thin core 102 (FIG. 1), often 200 nanometers or less thick, through thin lower cladding to a nearby photodetector 106, 108. The altered coupling results in changes in an effective leakage of photons from the waveguide into the photodetector. The waveguide may have lateral cladding 104 or other provisions to prevent lateral escape of light from the core. U.S. Pat. No. 8,349,605 ('605) teaches a LEAC sensor which employs either a single photodetector, or multiple photodetector segments 106, 108 separated by insulating regions 110, and as shown in '605 FIG. 8B. Such insulating regions have been implemented by etching a thin layer of photodetector material into isolated photodetector elements, and filling the intervening regions with an insulator.

The evanescent or evanescently coupled optical field of the LEAC sensor must have at least some overlap with the photodetectors in order to generate photocurrent. However, as the optical field impinges on photodetector 106, 108 and intervening insulator 110 material of different refractive index, some amount of light is reflected or scattered from the discontinuity in refractive index in a direction parallel to the waveguide core's 102 axis. The scattering of light is disadvantageous because it reduces the optical power remaining in the guided mode, reducing the magnitude of photocurrent generated by subsequent photodetectors. The scattering of light is also disadvantageous because it increases the background photocurrent in neighboring detectors by a mechanism other than the desired mechanism of evanescent coupling.

Fabrication of segmented photodetectors in a LEAC sensor can further lead to non-planar waveguides unless complex, and hence costly, fabrication is employed. When the insulation is deposited, typically with chemical vapor deposition or plasma enhanced chemical vapor deposition, to fill the etched regions between isolated photodetector elements, the insulating material is also deposited on top of the photodetector elements leading to a non-planar surface. In the prior art, chemical-mechanical polishing was used to make the surface planar prior to depositing more layers, such as lower cladding (not shown in FIG. 1) or core of the waveguide. Precision chemical-mechanical polishing requires specialized equipment and processes, and increases the complexity and cost of LEAC sensor fabrication.

SUMMARY

An analyte-detection system has an optical waveguide with first and second cladding layers adjacent a core; a light source coupled to provide light to the waveguide; a photodetector such as a metal-semiconductor-metal, vertical PIN, or horizontal PIN photodetectors, the photodetector having an absorber configured to detect light escaping from the waveguide through the first cladding layer; multiple, separate, photocurrent collectors, where each photocurrent collector collects current from a different portion of the photodetector absorber; and at least one current-sensing amplifier for receiving photocurrent. The photodetector absorber is an undivided absorber region for multiple photocurrent collectors. Either separate amplifiers are provided for each of the multiple photocurrent collection lines, or multiplexing logic couples selected photocurrent collectors to amplifiers, while coupling unselected photocurrent collectors to a bias generator.

A method of sensing concentrations of an analyte in a solution includes exposing a first cladding of a waveguide to the solution, the upper cladding being sensitized to the analyte; providing light to the waveguide; sensing leakage through a second cladding of the waveguide with a photodetector having a continuous absorber layer across several distinct portions of the photodetector; collecting current from at least one selected portion of the photodetector; and amplifying the collected current.

BRIEF DESCRIPTION OF THE FIGURES

FIG. 5 is a cross sectional view of a longitudinal portion of a LEAC sensor having multiple upper cladding regions differing in cladding material.

FIGS. 6A and 6B are illustrations of the local evanescent field effect by which optical leakage from the waveguide into the photodetector changes when refractive index of upper cladding changes.

DETAILED DESCRIPTION OF THE EMBODIMENTS

Figure 1:
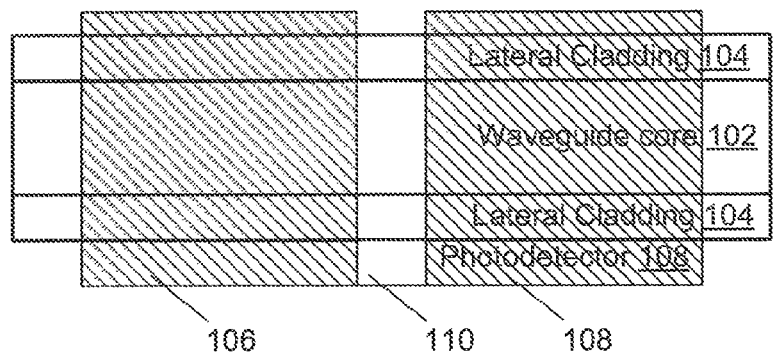
FIG. 1 is a top plan view of a LEAC sensor having a two-segment photodetector with segments separated by an insulator.

The present invention overcomes the disadvantages and limitations of the prior art by allowing a LEAC sensor with a continuous photodetector. The present invention also includes electronic circuitry for maintaining the electric field between the photodetector electrodes generally transverse to the photodetector axes.

A waveguide 152 (FIG. 2) is constructed over a linear, undivided, photodetector 154, such as a silicon photodetector. In an embodiment, photodetector 154 is curved into a spiral on a surface of a circuit. In alternative embodiments, other semiconductor photodetectors are used, the semiconductor being selected to have absorber-region bandgap energy less than the photon energy of the wavelength of light provided by photon source 151 to the waveguide. Here light is understood to refer to infrared, visible and ultraviolet radiation within the wavelength range of approximately 200 to 5000 nm and currently more preferably 400 to 2000 nm due to the maturity of photodetector and photon source technology at these wavelengths. While the photodetector 154 has a linear, undivided, absorber region 214 (FIG. 3) adapted to absorb photon leakage from core 206 through a lower cladding 204, and a linear, undivided, charge-collection region 216, the photodetector has separate output metal contacts 217, 156, 158, 160 or contact groups with each contact 156, 158, 160 (or group of contacts) coupled to separate amplifiers 162, 164, 166 through a separate photocurrent collection line. Amplifiers may be transimpedance amplifiers or current amplifiers or buffers or voltage amplifiers or buffers appropriate to an operating mode of the photodetector. The term amplifier as used in this document may also refer to electronic devices used for converting an electrical signal from a photodetector to a signal more appropriate for transmission to other electronic circuits or equipment. For example, for purposes of this document, an amplifier could include an electronic mechanism for measuring current and producing a digital signal such as an analog-to-digital converter or electron counting device. Since transimpedance amplifiers operate as a current to voltage converter, this provides separate voltage 168, 170, 172 outputs each associated with current collected at respective contacts 156, 158, 160 on each portion of the linear undivided photodetector 154, 216 charge-collector region. Since it is desirable to keep the voltage at each of metal contacts 156, 158, 160 the same to prevent current flow parallel to the axes of the photodetector absorber 214 and charge collection regions 216, each transimpedance amplifier biases the corresponding metal contact with a similar reference voltage. For example, a transimpedance amplifier based on an operational amplifier or other differential amplifier may be made to bias a metal contact connected to one of the differential inputs of the amplifier by connecting a reference voltage to the other differential input of the amplifier that is approximately equal to the desired bias voltage. As an example, a reference voltage of 2.5V may be used in conjunction with some metal-semiconductor-metal photodetectors.

The sensor also has a substrate 202 that forms a first side of P-I-N diode photodetector 154 having a full-length ground contact and metal 212, 176, or a linear array of smaller ground contacts with metal 212, a lower cladding 204, and an upper cladding 208 having some portions exposed to a solution. Upper cladding 208 may have portions that are sensitized to an analyte that may be present in the solution. In some particular refractometer embodiments, a fluid being sensed serves as part or all of upper cladding. Absorber 214 forms the intrinsic (I) region of the PIN photodetector, and the charge-collection region 216 forms a second side of the PIN photodetector. Passivation layer 220, and other oxide layers are provided to protect components of the LEAC sensor other than sensitized upper cladding 208 from the solution containing an analyte. In some embodiments sensitized upper cladding is formed of a material that changes refractive index and/or thickness when exposed to a particular analyte such as a solvent, in other embodiments sensitized upper cladding is coated with a substance, such as a protein, that alters its refractive index when exposed to a particular analyte.

It should be noted that the upper, or sensitized, cladding in particular embodiments has a protein layer adherent to it, the protein serving as a sensitizing agent. The protein is a particular protein selected to have binding sites configured to bind a particular analyte. Further, the protein may change refractive index when the analyte binds to it. Alternatively, the binding of an analyte that has a different refractive index than the media around the analyte displaces the media leading to a change in the refractive index in the vicinity of bound analyte. Refractive index changes may be due to displacement of media by analyte or protein configuration changes upon binding or both. In many particular embodiments, the protein is an antibody reactive to the analyte.

An alternative embodiment of the LEAC sensor has a waveguide 252 (FIG. 4) is constructed over a linear, undivided, photodetector 254, such as a silicon photodetector. Photodetector 254 has a long ground contact or array of contacts 255. A photon source 251 provides photons to the waveguide. While the photodetector 254 has a linear, undivided, absorber region adapted to absorb photon leakage from core 206 through a lower cladding 204 (FIG. 3), and a linear, undivided, charge-collection region 216, the photodetector has separate photocurrent collection lines 256, 258, 260, 262, each coupled to a group of metal contacts, with each photocurrent collection line coupled to a pass gate or switching devices 264, 266, 268, 270 configured to couple the photocurrent collection line and associated contacts or contact groups to one or more shared amplifiers. A decoder 272 drives switching devices 264. 266. 269. 270 to select one group of metal contacts or collection line of collection lines 256, 258, 260, 262 as input to a transimpedance amplifier 280. Decoder 272 has selection control inputs 273 that determine a currently selected collection line. Since it is desirable to keep the voltage at each photocurrent collection line 256, 258, 260, 262 the same to prevent current flow along the absorber and charge collection regions, each switching device 270, 264 is provided with an inverter 274, 278 driving an additional switching device 276, 282, to couple each photocurrent collection line 256, 258, 260, 262 that is not selected by decoder 272 to a bias voltage generator 284. Photocurrent collection lines are typically metal, but may be formed in another electrically-conductive layer. While N-channel pass-gates are illustrated, functionally similar multiplexing structures can be assembled from p-channel or full-complementary pass-gates with appropriate signal inversions and control as known in the art of integrated circuits. Transimpedance amplifier 280 provides a voltage output 287 indicative of photon leakage through the lower cladding for a selected photocurrent collection line 256 258, 260, 262 on photodetector 254.

Figure 4:
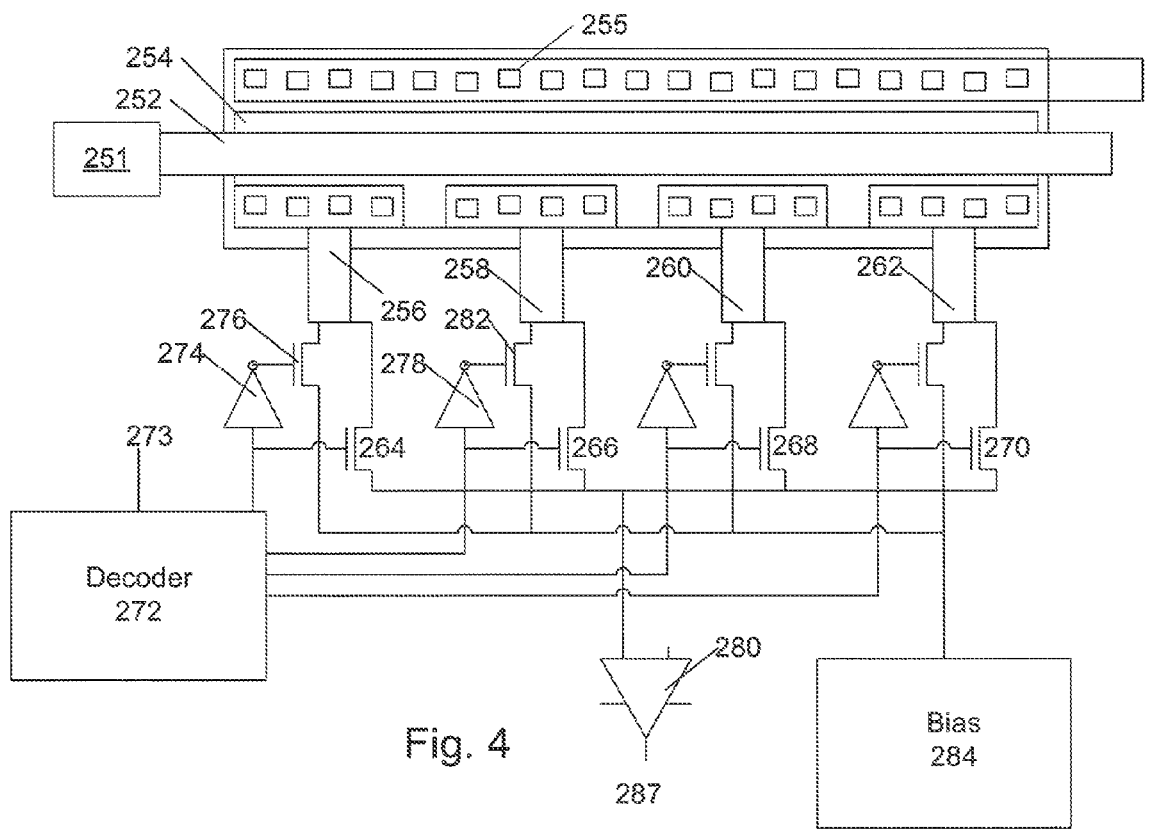
FIG. 4 is a top plan view of an alternative embodiment of a LEAC sensor having a continuous photodetector with a multiplexed sensing amplifier.
Figure 4A:
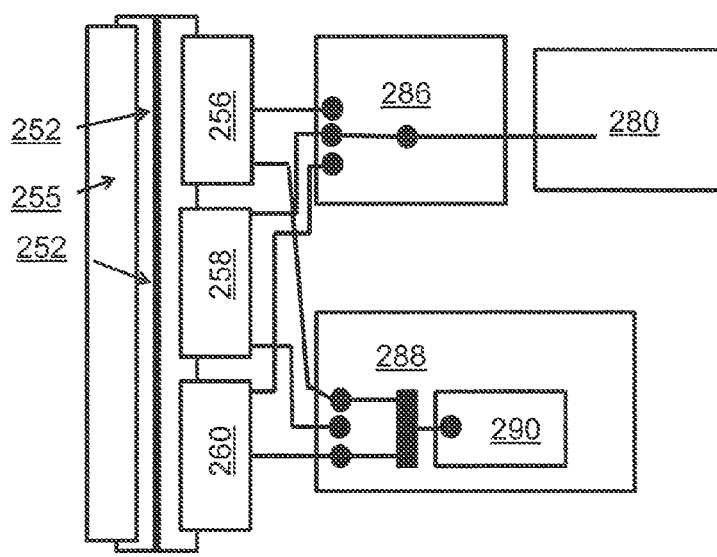
FIG. 4A is a block diagram illustrating significant points of the embodiment of FIG. 4.

Operation of the embodiment of FIG. 4 is best understood with reference to FIG. 4A. The pass-gates 270, 264, 266, 268 together with the decoder 272, form a multiplexor 286 that selective couples metal contacts or groups of metal contacts 256, 258, 260 to amplifier 280. The inverters 274 and additional switching devices 276, 282, form a biasing system 288 that couples each metal contact 256, 258, 260 that is not currently selected as input to an amplifier 280 to a bias generator 290.

In use, presence of analyte on sensitized upper cladding regions 208 causes a change in refractive index of the upper cladding. Since the waveguide core region 206 is thin, often less than 200 nm, a change in refractive index of upper cladding 208 causes a redistribution of electric field in the waveguide, including in lower cladding 204, and thus changes photon leakage through the lower cladding 204 into photodetector absorber region 214. Photon leakage may be caused by evanescent coupling of two higher, but not necessarily the same, refractive index layers, through a lower refractive index layer. Changes in photon leakage into photodetector absorber region 214 change photocurrent in the photodetector as collected by charge collector 216 and metal 217. Since metal 217 carries the photocurrent to the transimpedance amplifiers, the transimpedance amplifier voltage outputs 286, 168, 170, 172, therefore changes with changes to the refractive index of upper cladding.

In alternative embodiments, junction, metal-semiconductor-metal, or other types of photodiodes may replace the P-I-N diode described with reference to FIG. 2.

In an embodiment (FIG. 3A) using a metal-semiconductor-metal (MSM) photodetector, a semiconductor absorber layer 230 is grown atop an insulating layer such as an oxide 234, insulating oxide 234 in turn deposited or grown atop a supporting silicon wafer 232 or other substrate. Ground metal 212 forms an ohmic contact to absorber 230, and output metal contact 217 forms a Schottky diode to the semiconductor absorber 230 that serves as a charge-collection region. Other circuitry and components of this embodiment of the LEAC sensor are similar to those for the PIN diode embodiment of FIG. 3. While P-I-N detectors may be operated with little or no applied bias, symmetric MSM photodetectors are operated with voltage bias. Depending on photodetector absorber 230 material and voltage bias, MSM photodetector may function as a photodiode or photoconductor with effects on speed and noise as known by those who practice the art of photodetector engineering.

In all embodiments, output metal contacts 217, 256, 258, 260, 156, 158, 160 and photodetector "ground" contacts 176, 255, 212, are positioned sufficiently far from the waveguide that these contacts do not cause significant scattering of light in the waveguide. It is preferable that scattering from this source be less than 1 decibel per centimeter of waveguide length. In some embodiments, output contacts have a short transparent conductor, such as an indium tin oxide layer, intermediary between metal and absorber or charge-collector diffusions to help reduce scattering by output contacts.

In an embodiment (FIG. 3B) using a lateral P-I-N photodetector, a semiconductor absorber layer 238 is grown atop an insulating oxide 234, insulating oxide 234 in turn deposited or grown atop a supporting silicon wafer 232. Ground metal 212 forms an ohmic contact to a region, such as a P type region, 236 diffused or implanted into absorber 230, and output metal contact 217 forms an ohmic contact to a second region, such as an N-type region 240, that serves as a collector common or ground contact and charge collector region on an opposite side of the waveguide and also diffused into semiconductor absorber 238. The second diffused region 240 serves as an output charge-collection junction region. N-type regions 240 and P-type regions 236 may be continuous parallel to axis of photodetector or preferably may be segmented to reduce possible current flow between neighboring metal contacts 240, 236 that could result from small differences in voltage bias applied to neighboring metal contacts. N and P regions 236, 240, are typically located far enough from the waveguide that their segmentation does not cause significant scattering of light in waveguide. Other circuitry and components of this embodiment of the LEAC sensor are similar to those for the PIN diode embodiment of FIG. 3.

A continuous photodetector has three or more groups of output contacts where the output contacts are connected to amplifiers or switching circuitry used to read out each group of contacts. Each group of output contacts is held at close to the same voltage as all the other groups. The continuous photodetector is proximate to an optical waveguide evanescently coupled to the photodetector so that when optical power, whether in the visible, infrared or ultra-violet, all of which are defined as light for the purposes of this document, flows generally in the direction of the axis of the waveguide at least some fraction of the optical power is absorbed by the photodetector. Light carried by the photodetector results in photocurrents at locations along the continuous photodetector dependent on analyte concentration and particular sensitization of the upper cladding 208. The photocurrents change with presence of one or more analytes adjacent a sensitized cladding of the waveguide because of changes to the refractive index of upper cladding 208. The device may also be structured as a refractometer to measure the refractive index or changes in the refractive index of a sample without a sensitization layer. The waveguide may be strongly coupled to the photodetector as would be appropriate for converting a substantial portion of the light to an electrical signal in a small area, or it may be weakly coupled to the photodetector to allow the absorption process to be spread across a wider area. The later situation is, for example, employed in the local evanescent array coupled sensor, as has been described in publications by at least one of the inventors and are hereby incorporated by reference to provide context for the application of the current invention as an improvement to that and similar sensors.

A benefit of the continuous photodetector is that it may reduce the scattering loss compared to photodetector arrays that have electrically isolated elements where the electrical isolation is accomplished by etching away portions of the photodetector material and refilling it with insulating material because such insulating material also has different optical properties, such as refractive index or absorption, and thus causes the optical field within the photodetector, insulating material, cladding, or core and hence light within the waveguide to diffract or scatter from the waveguide or photodetector. The continuous photodetector may also be easier to fabricate than a segmented photodetector array, particularly so if chemical-mechanical polishing steps may be eliminated.

An optical waveguide sensor such as the LEAC sensor contains multiple regions some of which are exposed to a sample to be interrogated and sensitized to a first analyte, and some control regions not exposed to the sample. The control regions not exposed to the sample are used as reference regions to compensate measurements for changes in the measurement or sensor system including but not limited to optical source power or optical source to waveguide coupling efficiency that alter the photocurrents produced in the photodetectors but are not associated with the desired property of the sample. Rapid switching between control and reference regions may provide an AC signal dependent primarily on analyte concentration that can be amplified readily. Alternatively, electronic amplification or signal processing channels may be dedicated to one or more reference regions and independently to one or more sample sensing regions to allow simultaneous data acquisition of reference and sensing signals.

Figure 2:
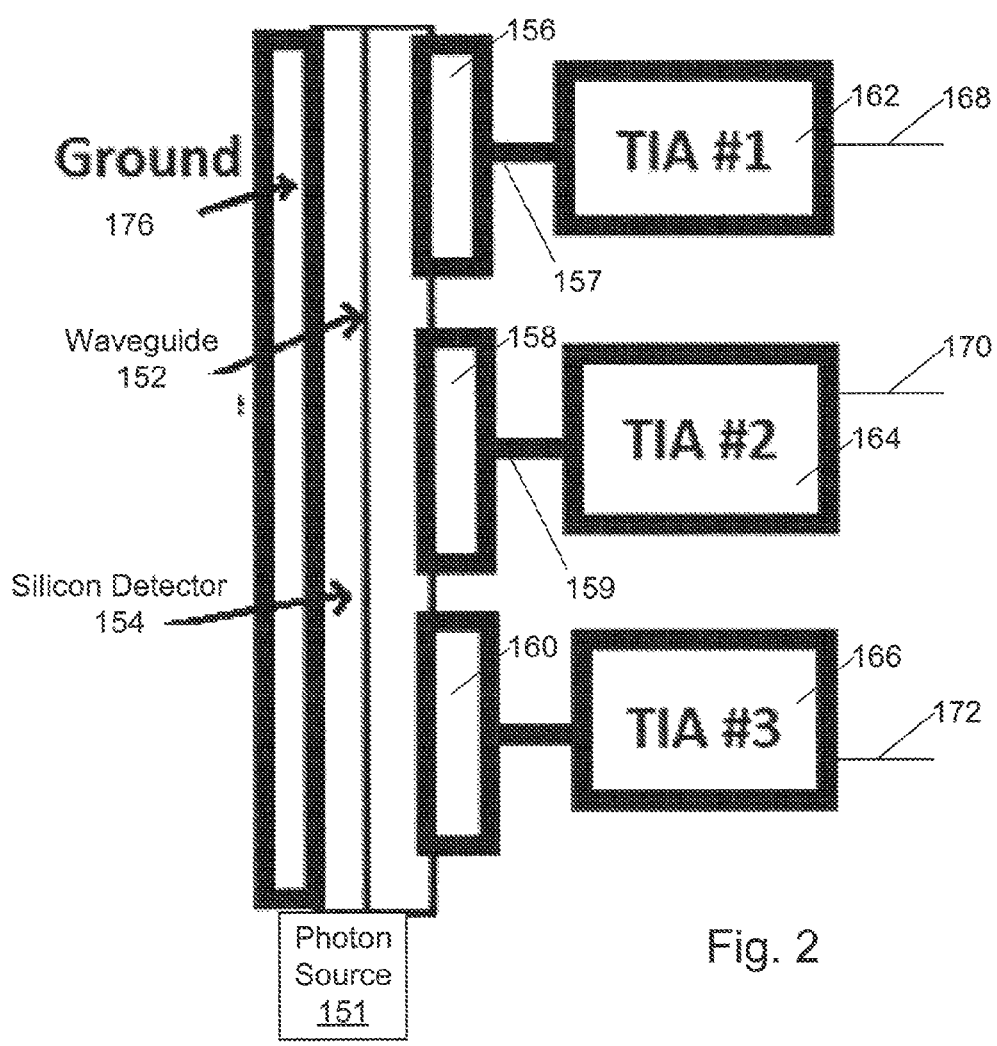
FIG. 2 is a top plan view of a LEAC sensor having a continuous photodetector with multiple sensing amplifiers.
Figure 3:
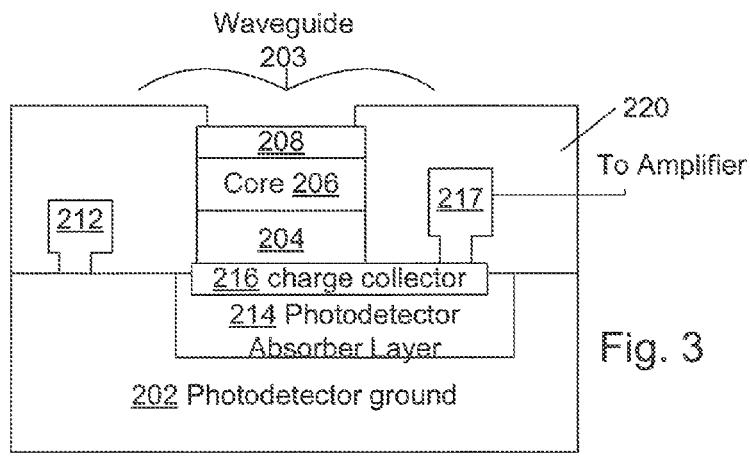
FIG. 3 is a cross sectional view of a portion of a LEAC sensor of FIG. 2 or 4.

In an alternative embodiment, the LEAC sensor has multiple regions, some of which are control regions not exposed to the sample, some of which are sensitized to a first analyte and exposed to the sample, and some of which are sensitized to a second, third, or in some embodiments a fourth or additional, analyte and exposed to the sample; rapid switching using a multiplexor on outputs of sensors according to an embodiment resembling FIG. 2, or rapid switching of the decoder and switches of embodiments resembling FIG. 4, may provide an AC signal dependent primarily on analyte concentration for a particular analyte of the first, second, third, fourth, or additional analytes that can be amplified readily, and select between analytes to time-division multiplex the AC signal among analytes.

In some embodiments, a LEAC sensor of a type according to FIG. 2 or FIG. 4 has individual regions having different upper cladding materials as illustrated in FIG. 5. In this embodiment, a high-index waveguide core layer 302 has a lower cladding 304 above a photodetector 306. A first upper cladding material 308 is lies over a portion of the photodetector 306, and a second upper cladding material 310 lies over another portion of the photodetector 306. In a particular embodiment both upper cladding material's thicknesses are the same and about 2 microns. In another particular embodiment, the first cladding material is a solid of about 2 microns in thickness and the second cladding material is a fluid of about 100 nm or more in thickness. The combination of a solid first cladding material of relatively fixed refractive index and a fluid second cladding material of potentially varying refractive index is useful for measuring the refractive index of the fluid second cladding material with respect to the solid first cladding material, which may serve as a reference region.

To minimize the undesired aspect of reflection and scatter at the interface of two such regions with different upper claddings 308, 310, it is desirable for the two regions to have similar upper cladding refractive indices even if the two regions have different materials for the upper cladding or serve different purposes as is the case for reference and sample regions. Thus it is desirable to have upper cladding materials in reference regions with refractive indices comparable to those of potential samples of interest. Samples that are principally water may have a refractive index near 1.33 and thus an upper cladding material of Teflon for the associated reference region could help reduce the interfacial mismatch of the modes between the two regions. Another sample of interest might be liquid or deposited hydrocarbons such as oils. Some oils have refractive indices near 1.45 and thus an upper cladding material of silicon dioxide for the associated reference region could help reduce the mismatch of the optical mode as light carried along the waveguide transits from the reference region to the sample or the sample to the reference region. Other samples of interest are known to those skilled in the art of applications of refractive index sensors and other materials of similar refractive indices to the samples of interest are known to those skilled in the arts of materials science. The embodiments offered here are examples of the invention and are not limitation.

Consideration of Upper Cladding Materials and Refractive Indices to Reduce Scattering Losses and Provide Reference Regions Suitable for Various Analytes and Sample Matrices Note that scattering here may be used as a term to describe loss of light from total internal reflection or waveguide mode confinement due to the roughness of optical core layers, cladding layers or the interface between them or scattering may be used to describe a large difference in mode profiles with smaller than desired overlap that causes poor transmission of light from one region to another. Those skilled in the art of waveguide design and coupling will understand the importance of mode-matching and that mode profiles can be altered by changing layer dimensions and compositions that affect refractive index while also needing materials with low absorption loss. When transitioning from oxide to an aqueous sensing region, the propagating mode has reduced transmission through the oxide/water boundary. However, when working with a system that is closer to index-matched, for example in one embodiment by using Teflon instead of oxide, light more readily propagates from the Teflon reference region into the oxide sensing region.

For some sample fluids, for example oils with refractive indices near 1.4 to 1.5, it may be advantageous to use silicon dioxide or other low optical loss materials with a refractive index of approximately 1.45 as the upper cladding for the reference region prior to the sensing region. For sensing other sample fluids, such as aqueous ones with refractive indices near 1.3 to 1.4, it may be advantageous to use Teflon or other low refractive index polymers as the upper cladding material in the reference region. Keeping the refractive index of the upper cladding in the reference region close to the refractive index of the sample in the sensing region improves optical coupling as light transitions from a reference region to a sensing region or from a sensing region to a reference region. Other approaches that may be used alone or in conjunction with selecting near matching refractive indices for the reference region upper cladding include gradually tapering the transition from the reference region to the sensing region. Such tapers may be symmetric about a vertical plane containing the waveguide axis or they may be asymmetric to simplify alignment of features in a cladding layer to the core layer. The angles of symmetric or asymmetric tapers may be designed to achieve desirably low reflection coefficients using simulation tools including beam propagation and finite difference time domain electromagnetic modeling software. In general, the length of the waveguide over which the taper occurs should be at least many wavelengths.

Teflon AF Processing

Methods for depositing, patterning, curing and enhancing properties of cladding and core films are taught by materials manufacturers and providers. For example, methods and products for promoting the adhesion of Teflon AF films are provided by DuPont and its agents. Further, experience in processing the films suggests certain protocols that can aid their application to constructing layers for optical waveguide sensing devices.

Example Adhesion Promoter Preparation Protocol

Teflon adhesion promoter has a short shelf life. As such, a fresh batch should always be made as the promoter can spoil in less than 24 hours. The adhesion promoter is a fluorosilane in a solution of 100% ethanol, methanol, and DI water. The adhesion promoter solution is prepared using the following procedure.

In a clean glass bottle, prepare in the following proportions.

Add 18 mL 100% ethanol using a pipette
Add 1 mL of DI water using a pipette
Add 1 mL of methanol using a pipette.
Lastly, add 0.5 mL of 1H,1H,2H,2H-Perfluorodecyltriethoxysilane, 97% (Alfa Aesar #L16585).

Screw the cap onto the bottle and shake the solution lightly for several seconds. The Teflon AF adhesion promoter solution is now ready to be used.

Adhesion Promoter Spin-On and Bake

Spin the adhesion promoter onto the sample at 2000 RPM for 30 seconds.

Place the sample on a hot plate set to 110 C for 5 minutes. Remove the sample and let it cool for 1 minute.

Adhesion Promoter Spin-On and Cure

Place the sample onto the spinner. Apply Teflon AF so there are no bubbles. Bubbles will cause the film to spin on non-uniformly. Start the spinner at 500 RPM and ramp up to 1000 RPM. Let spin at 1000 RMP for 60 seconds. To create a uniform film, the Teflon film should be heated slowly to avoid rapid evaporation.

Place the sample on a hot plate set to 60 C. Ramp up to 80 C and let it cure for 3 minutes.

Transfer to a hot plate set to 120 C. Let cure for 1 minute. Then ramp up to 180 C. Let cure for 3 additional minutes.

Transfer to a hot plate set to 250 C and let cure for 10 minutes.

Teflon Photolithography and Etching

In order for photoresist to adhere to Teflon, the Teflon film should be plasma treated. Liquid adhesion promoters should not be used. Instead, to improve adhesion, oxygen plasma etch at 40 sccm/40 Watts in a reactive ion etcher for 5 to 15 seconds. Remove the sample and spin on positive photoresist at 6000 RPM for 30 seconds. Bake on hotplate at 100 C for 2 minutes. Then using the Teflon AF mask, align the sample and expose for 20 seconds (260 mJ/cm$^2$ total irradiation). Then develop the photoresist using the appropriate liquid developer. Next, oxygen plasma etch the sample for 5 minutes at 40 sccm/40 W in reactive ion etcher to etch away unwanted Teflon. Teflon etches in oxygen plasma at roughly 600 nm/minute at 40 sccm/40 W.

Final Cleaning

First, rinse the sample with acetone, methanol, and DI water to remove any remaining photoresist. Then sonicate in acetone for 5 minutes. Sonicate in methanol for 5 minutes, and lastly rinse in DI water for 5 minutes using a clean beaker. As a final cleaning step, the sample may be briefly oxygen plasma cleaned in a reactive ion etcher.

Working Principle: Local Evanescent Field Shift Effect

The local evanescent field shift effect by which the LEAC sensor operates is illustrated in FIG. 6. In part due to the nanoscale dimensions of the waveguide core, there is a significant interaction between the guided mode's evanescent tail and the upper cladding medium above the waveguide core. As the refractive index in the medium above the waveguide increases, either due to a change in bulk refractive index of upper cladding or analyte binding to probe molecules at the core/upper cladding interface, the evanescent field is shifted up and away from the integrated Si photodetector, producing less photodetector coupling, and therefore a decrease in the measured photocurrent. The chip can be functionalized for multi-analyte sensing by patterning different probe molecules on the upper cladding in distinct regions of the waveguide.

Fabrication Tolerances and Scattering

Analytical scattering loss models have been applied to understand the effect of device fabrication tolerances on waveguide scattering losses. In general, both sidewall scattering and surface roughness loss increase with both autocorrelation length $L_c$ and RMS surface roughness $\sigma$. The models indicate that scattering losses of approximately 1 dB/cm or less could be achieved in a modern semiconductor fabrication facility using high quality optical films. A reduction in scattering loss could improve the sensor's sensitivity or its dynamic range.

Development of a Portable Prototype

Figure 8:
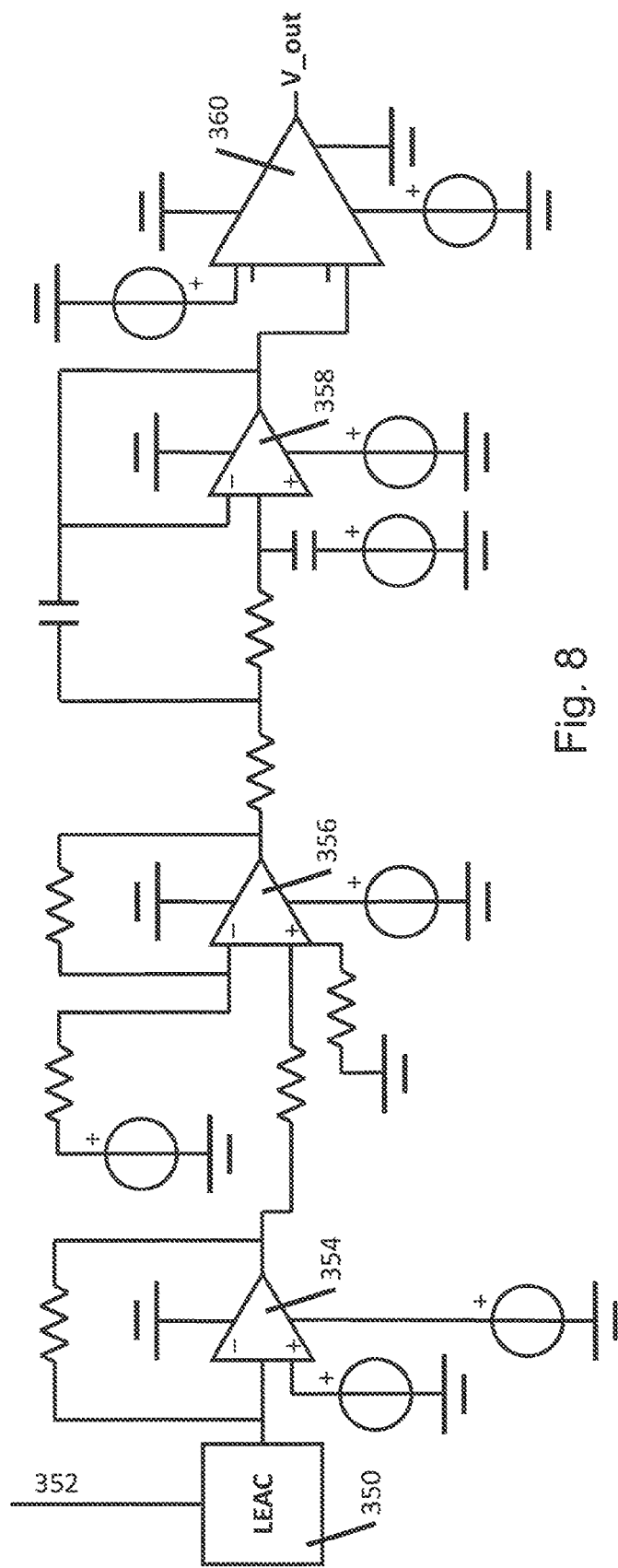
FIG. 8 is a schematic of a prototype card having a LEAC sensor according to FIG. 2 or FIG. 4 and associated amplification electronics.
Figure 10:
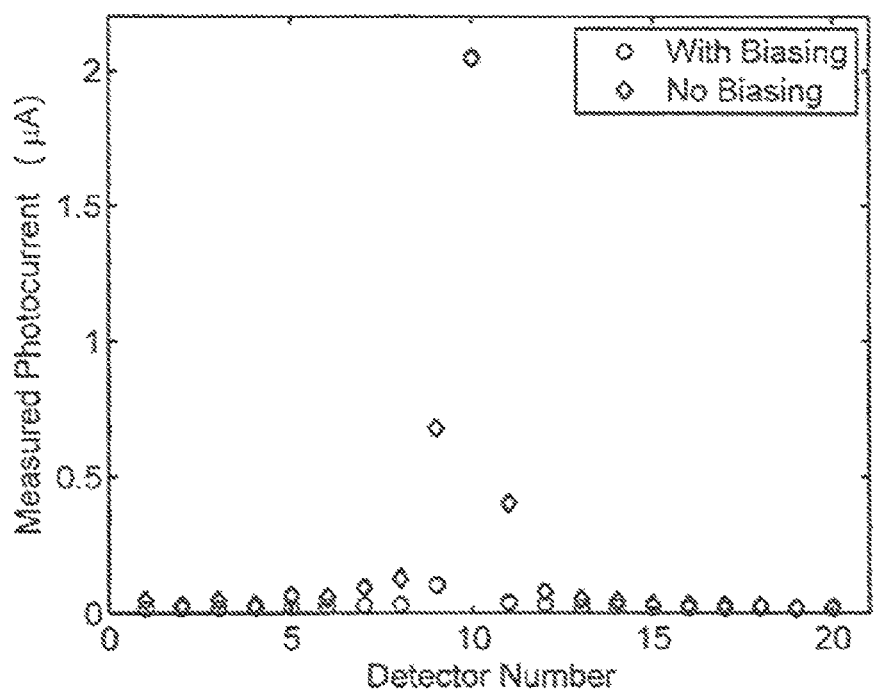
FIG. 10 is an illustration of the effectiveness of the bias circuitry in minimizing interference to photocurrent in a photocurrent collection line from light reaching a portion of the continuous absorber associated with another photocurrent collection line.

A portable prototype with attached fluidics has been developed on an adapter card using a LEAC chip with a multiplexer of the type described with reference to FIG. 4, the board having a schematic according to FIG. 8. LEAC sensor 350 is provided with multiplexer selection inputs 352 for determining a selected portion, or group of contacts, of the continuous photodetector. Photodetector output passes through transimpedance amplifier 354, gain stage 356, pulse shaper 358, and output stage 360 to provide an output signal representative of analyte concentration adjacent Photocurrent Localization Biasing Circuit In a multiplexed embodiment, a biasing circuit of the type illustrated in FIG. 4 is employed to both measure the localized photocurrent for each individual detector in the continuous photodetector array and allow an optically smooth core/cladding interface. The photocurrent localization circuit works by effectively sweeping away carriers generated in the vicinity of contact groups other than those being measured at a particular point in time, so that they are not collected by the contact group being measured. Carriers generated in the vicinity of a contact group being measured are collected and converted to voltage using a transimpedance amplifier (TIA), such as one with a gain of 2V/μA. Note that the photocurrent is better localized when the biasing circuit is used as seen in FIG. 10, as higher photocurrents are measured on adjacent detectors when the biasing circuit is not used.

Real-Time Refractive Index Sensing Results

Figure 9:
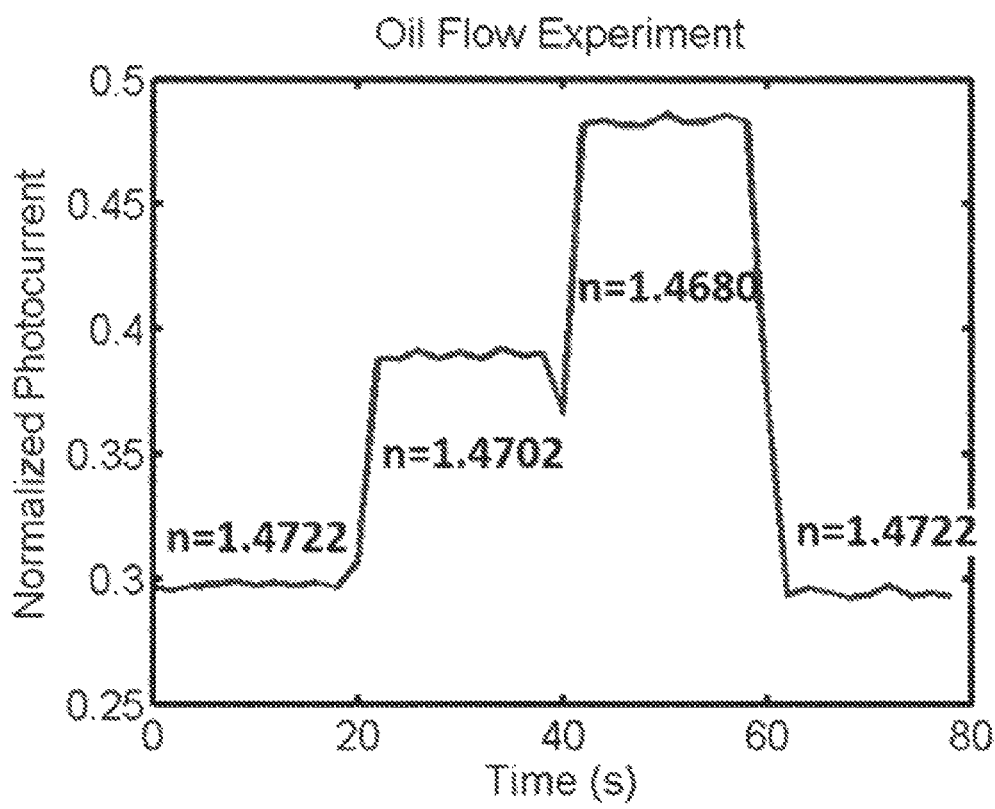
FIG. 9 in illustration of output from the LEAC sensor used as a dynamic refractometer, measuring refractive index of an oil flowing over the sensor.

FIG. 9 illustrates use of the sensor as a dynamic refractometer for oils of different compositions and thus different refractive indices flowing past the sensor. The photocurrent increases as fluids of decreasing refractive index flow through the channel. The photocurrent returns to its initial value when sesame oil (n=1.4722) returns to the channel. Real-time data have been observed to be noisier than the static measurements due to limitations in the optical coupling configuration used for this specific measurement, but this is not considered to be a fundamental limitation. For real-time sensing, the minimum resolvable change in photocurrent demonstrated so far is $4.1 \times 10^{-5}$.

Light Sources

The LEAC sensors herein described require that light, whether infrared or visible, be propagating through the waveguide, since it is leakage of this light from the waveguide into the photodetector, also called a photosensor, that is detected by the photodetector. It is anticipated that this light may originate from a light emitting diode (LED), laser, or other solid state, compact light source integrated on the same wafer as the LEAC sensor, in alternative embodiments from a separate LED, laser or compact solid-state light source and coupled into the waveguide. In a particular embodiment, it is anticipated that the light is coupled into the waveguide by a grating-type coupler integrated on the same wafer as the LEAC sensor. Light may also be coupled into the waveguide using guided wave optics such as fibers, graded index optics or classical optics as well known in the art of optical waveguide and fiber optic coupling from and to components.

An operating principle behind the LEAC biosensor is the local evanescent field shift effect, whereby the guided mode in the waveguide core is shifted upward in response to an increase in the refractive index of the upper cladding sensing region. As a result of the field shift, there is less coupling between leaky modes and the underlying photodetector. The decrease in photodetector coupling corresponds to a decrease in the measured photocurrent.

2. Primary Sensing Mechanism

One sensing mechanism of the LEAC chip is the local evanescent field shift effect. Due to the nanoscale thickness of the waveguide core, coupled light is weakly confined, so there is a strong interaction between the mode's evanescent tail and the structure's upper cladding. In response to an increase in upper cladding refractive index, the evanescent field shifts up and away from the photodetector, resulting in less photodetector coupling loss and a corresponding decrease in the measured photocurrent in the underlying photodetector. This effect is illustrated in FIGS. 6A and 6B, which is a cross-sectional view of the waveguide structure with core 601, field intensity plotted as 604 with high refractive index upper cladding 608, resulting in low intensity of field at photodetector absorber 614; and field intensity plotted as 602 with low refractive index upper cladding 606, shown over constant refractive index lower cladding 610, resulting in relatively high intensity of optical field at photodetector absorber 612. The field is shifted upward and there is reduced interaction of the evanescent field with the integrated photodetector when n=1.4722; however there is greater interaction when n=1.4680. As such, photodetector coupling is much higher for n=1.4680. In FIGS. 6A and 6B, substrate is shown as 616, and an oxide isolation 618 is shown between substrate and absorber 612.

From a theoretical standpoint, this effect can be analytically derived for a planar asymmetric waveguide structure where the lower cladding decay constant $\gamma_{lc}$ is given by $$\gamma_{lc} = \frac{2\pi}{\lambda}\sqrt{n_{\mathit{eff}}^2 - n_{\mathit{lower\ cladding}}^2}\ .$$

As the upper cladding refractive index increases, the effective index of the propagating mode, $n_{\mathit{eff}}$, increases, and thus $\gamma_{lc}$ increases. Therefore, the lower cladding effective penetration depth $d_{lc}=1/\gamma_{lc}$ decreases and there is less photodetector coupling. For the LEAC structure, upper cladding-dependent photodetector coupling, and thus the coupling losses to the photodetector absorber, constitutes an optical signal. For biosensing applications, analyte binding of proteins in an aqueous media in the upper cladding sensing region would produce an increase in refractive index, so analyte binding would be transduced as a decrease in measured photocurrent.

3. Device Fabrication and Photocurrent Localization Biasing Circuit

Figure 3A:
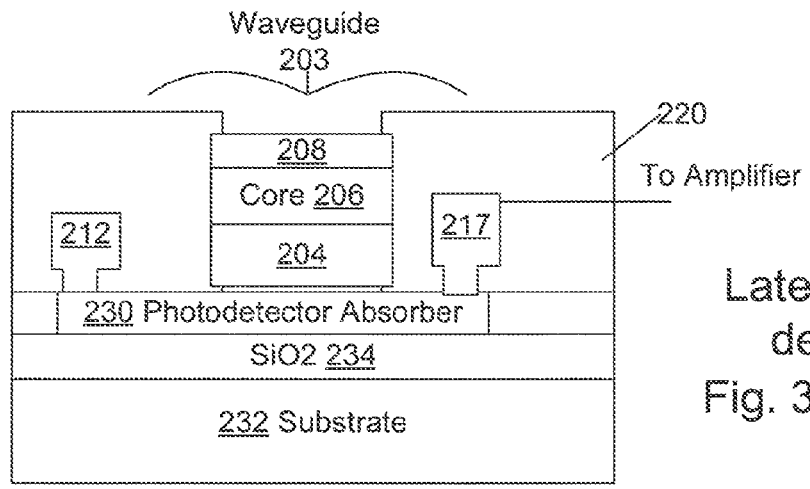
FIG. 3A is a cross sectional view of an alternative embodiment of the LEAC sensor using a metal-semiconductor-metal photodetector.

In one embodiment, LEAC chips have a metal-semiconductor-metal photodetector resembling that of FIG. 3A and configuration resembling that of FIGS. 4 and 4A are fabricated. A p-type <100>, 100-200 ohm-cm, Silicon-On-Insulator (SOI) wafer with a 10 μm device layer (Ultrasil, Hayward, Calif.) is used as the starting substrate. As a convenience for small scale single chip-at-a-time fabrication, the wafer may first be diced into approximately 1×1 cm chips and thoroughly cleaned using the RCA process. Alternatively a similar process flow to the following may be implemented to process whole wafers. Further processes capable of realizing structures used for the invention are known to those practiced in the art of integrated circuit, microelectronic, microfluidic, and silicon photonics fabrication.

3.1.1 Photodetector Fabrication

An embodiment of a LEAC chip having a lateral metal-semiconductor-metal photodetector is fabricated with integrated photodetector structure may be fabricated as follows. A low-temperature (<250°) process may be employed if necessary to avoid or reduce degradation of the chip's metal-semiconductor-metal contacts so that the photodetectors dark current would increase or become less stable or more temperature sensitive. It has been found that high quality films may reduce leakage currents due to pinholes and reduce layer surface roughness that increases optical scattering. Initially, approximately 300 nm of high-quality $SiO_2$ is deposited with a PECVD system. Next, using photolithography masking and conventional oxide etching techniques, a window is etched in the oxide layer revealing an approximately 50 μm×6 mm strip of Si. Wet etching can provide reduced surface roughness of the Si revealed in the window. Using a liftoff process, Ti/Al metal contacts are e-beam evaporated to partially overlap the Si, with the remainder of the metal film forming an interconnect line on the $SiO_2$. As an example, the liftoff process may be used to pattern 20 separate contacts to each be connected to amplification, multiplexing or other readout circuitry. Depending on the oxide thickness and etch profile, step coverage may be improved by depositing metal contacts that are thicker than the oxide window ($SiO_2$) layer. Each metal contact overlapped an area of (100 μm×30 μm) of the silicon photodetector absorber layer, which in this case is the device layer of the SOI wafer. In the evaporation step, Ti/Al are also used to form the chip's metal interconnects and probe pads.

3.1.2 Waveguide Fabrication

After fabrication of the integrated photodetector array, the waveguide structure is fabricated. An optional 20 nm layer of $SiN_x$ may be deposited to form a passivation layer. Then a layer of $SiO_2$ with a thickness $t_{oxide}$ is PECVD-deposited to form the waveguide's lower cladding. In an alternative embodiment, the lower cladding may also be created by thermally oxidizing the exposed silicon. Thermally oxidized silicon has been found to give lower waveguide loss than moderate quality PECVD-deposited oxide which may be more porous or have less optimal stoichiometry. After lower cladding deposition or growth, the waveguide core is fabricated by PECVD deposition of a thin layer of $SiN_x$ with a thickness of $t_{nitride}$. Standard photolithography and etching steps are used to form a ridge waveguide with width w and height H. The precise lower cladding oxide thickness, $t_{oxide}$, and waveguide core dimensions (w, $t_{nitride}$, H) can impact device sensitivity. For reference, dimensions used in one embodiment are $t_{oxide}$=1250 nm, $t_{nitride}$=H=40 nm, and w=7 μm. It may also be useful to use narrower waveguides to maintain a single mode field profile in the lateral direction. Electromagnetic waveguide modeling software may be used to determine other useful dimensions of the core thickness, width and the cladding thickness. Further discussion of electromagnetic simulations appears below. Silicon nitride and other materials used for the core may be completely removed or only partially etched to provide lateral confinement of the optical mode in the waveguide.

To reduce absorption and scattering losses a PECVD nitride deposition technique first described by Gorin et al. was employed to deposit a highly transparent ($\alpha$<0.1 dB/cm), relatively low index (n=1.8) $SiN_x$ film for the waveguide core. Also, the waveguide width w was increased to 7 μm compared to the smaller widths used in prior work. Wider waveguides have lower sidewall scattering loss for the fundamental mode although to wide of waveguides can allow multimode operation. For w=7 μm, losses of ~10 dB/cm were measured. Reduced roughness of the core sidewalls and surface can also reduce scattering loss.

3.1.3 Reference Region Fabrication

Figure 3B:
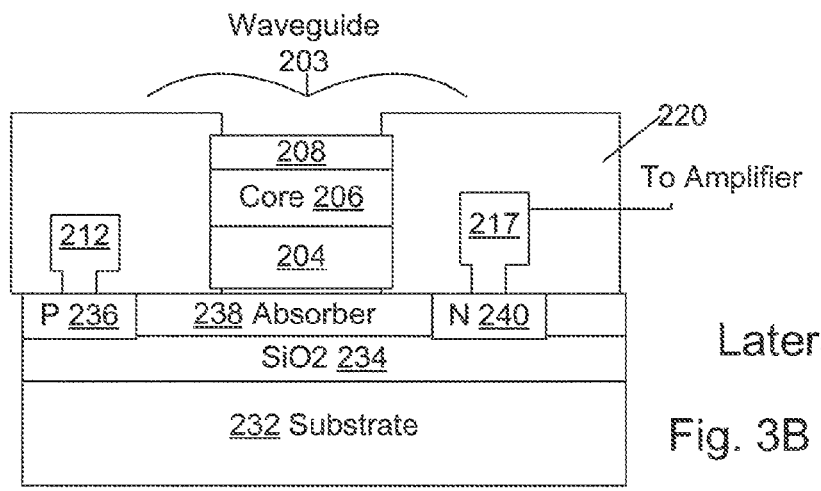
FIG. 3B is a cross sectional view of an alternative embodiment of the LEAC sensor using a lateral P-I-N photodetector.

Next, a 2 μm thick layer of upper cladding oxide was deposited in the region of the waveguide corresponding to photodetectors #1 to #5, by low-temperature PECVD oxide deposition followed by a photolithographic liftoff process. This step is used to establish an upper cladding reference region of fixed refractive index (n=1.454 at one operating wavelength of approximately 650 nm) along the waveguide. The reference region may be positioned so that waveguide light encounters it either before or after the sensing region. Multiple sensing regions may have intervening reference regions. If the change of the refractive index in the sensing region is significant or the loss of the sensing region changes due to absorption by the analyte or other interactions in the sensing region, it may be preferable to place the reference region upstream from the sensing region to reduce the complexity of using the reference region signal to normalize or otherwise manipulate the signal from the sensing region. The reference region may be used to normalize for fluctuations of the coupled light intensity into the sensing region. After reference region upper cladding deposition, only some photodetectors are exposed to the analyte, as they are not covered with oxide. In the example discussed here, photodetectors #6 to #10, corresponding to five more metal contacts on the absorber layer, were not covered with the upper cladding oxide. The oxide upper cladding serves an additional purpose. For real-time sensing, a flow cell is clamped onto the chip, one edge of which crosses the waveguide in the region between the polished edge of the chip and the sensing region. A 2 micron thick oxide layer is sufficient to reduce the evanescent field from appreciably interacting with the portion of the flow cell wall in contact with the chip and prevent the flow cell from scratching and permanently damaging the optically important portion of the waveguide. Additional fluid tight layers could also be introduced to cushion or secure the mechanical interface between the flow cell and the chip. After reference region patterning, the edge of the chip in one embodiment is polished to enable end-fire coupling with a 4/125 μm single-mode visible fiber excited by a 30 mW, 654 nm laser diode. Lastly, a CNC-machined polycarbonate flow cell with a soft Viton gasket is clamped onto the chip to permit syringe-driven fluidic flow, as shown in FIG. 3b. A bonding technique using SU8 epoxy-based photoresist can also be used to implement a portion or majority of a flow cell. Other techniques for connecting a macrofluidic or microfluidic flow cell to a sensor chip are known to those practiced in the art of microfluidic sensor construction.

3.2 Photocurrent Localization Biasing Circuit

Implementing a continuous photodetector absorber layer could reduce the ability to resolve neighboring regions along the photodetector compared to the segmented photodetector of the prior art unless circuitry is used to maintain the electric field in the photodetector generally perpendicular to the photodetector axis. In particular, biasing of a single contact or current collection line on the photodetector while not similarly biasing neighboring contacts causes the biased contact to collect photocurrent generated closer to neighboring unbiased contacts or current collection lines. Accordingly, a biasing circuit is employed to better localize the collection of photocurrent to regions closest to the contact. FIG. 4a is a functional diagram of the photocurrent circuit interfaced to three representative detectors on the chip. All detector pads except ground pad 176, 255 are held at similar bias voltages. The photocurrent localization circuit effectively sweeps away electronic carriers, holes and electrons, generated in the vicinity of detectors #1 (256) and #3 (260), so that they are not collected by detector #2 (258). Carriers generated in the vicinity of detector #2 are collected and converted to a voltage using TIA 280.

FIG. 10 demonstrates the photocurrent localization capabilities of a biasing circuit. A single mode fiber was placed directly on top of detector #10 so that light emanating from the fiber was received near detector #10, causing the reading from that detector to be saturated. When the biasing circuit is not used, significant photocurrents are measured on adjacent detectors as seen in particular with the diamond symbols for detectors #9 and #11 in FIG. 10. However, when the biasing circuit is turned on, the photocurrent from those two detectors drops significantly as shown by the circle symbols in FIG. 10.

4. Waveguide Structure Optimization

Simulations to Improve Device Sensitivity

Figure 7A:
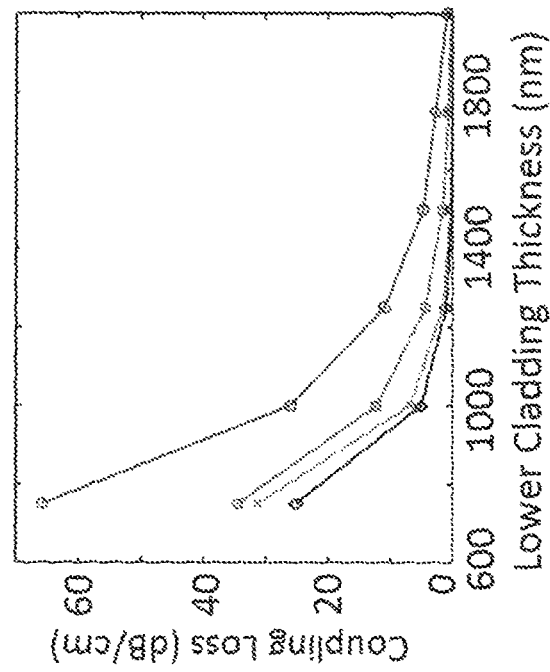
FIGS. 7A and 7B are illustrations of simulated thicknesses of lower cladding materials beneath the waveguide.
Figure 7B:
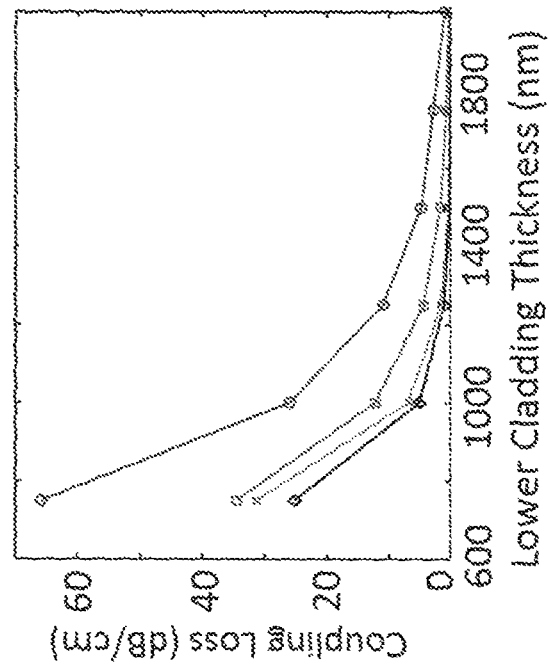

FIGS. 7A and 7B are derived from a full-vector, finite-difference mode-solver used to guide design of dimensions of the core and lower cladding, in order to improve device sensitivity. Results indicate a difference in photodetector coupling loss of 18 dB/cm can be achieved for n=1.46 vs. n=1.47. In general, sensitivity is improved by driving the waveguide closer to cutoff and reducing lower cladding thickness. However, there is a design tradeoff. As the lower cladding becomes thinner, photodetector coupling losses rapidly increase, which reduces light propagation to downstream detector regions. Given the design tradeoffs, $t_{oxide}$=1250 nm and H=40 nm were chosen for fabrication dimensions. Such a waveguide was simulated to produce losses of 6.2 and 3.6 dB/cm for upper cladding indices of 1.46 and 1.47, respectively.

4.2 Mode Matching for Transmission and Sensing

Modal simulations also indicate that mode matching, and hence index-matching at the upper cladding reference region/detector region interface useful to enhance adequate light propagation down the waveguide. The power transmission P at each interface is computed by calculating the square of the mode overlap integral (Eq. 1).

$$P = \left[ \frac{\int |E_1^* E_2| dA}{\sqrt{\int |E_1|^2 \int |E_2|^2 dA}} \right]^2 \quad \text{(Eq. 1)}$$

For a reference region upper cladding of n=1.46, power transmission is well over 95% if the index is matched within 0.02 RIU. However, notice that for a predominately aqueous detector region (n=1.33), the power transmission is only 60%.

Ideally, the refractive index of the reference region should be slightly lower than the anticipated refractive index range for the detector region. For close index matching, nearly 100% of the light will be transmitted; however there will still be an effect on the measured photocurrent in the sensing region, as the photocurrent in the sensing region is normalized with respect to photocurrent in the upstream reference region, such that $I_{normalized}=I_{sensing}/I_{reference}$.

If the reference region has a lower refractive index, the transmission effect can be used as a second sensing mechanism to work in concert with the local evanescent field shift mechanism. For example, as the refractive index of the sensing region is increased, the measured photocurrent would decrease as a result of less optical power transmission into the region and the evanescent field shift effect. In contrast, if the reference region has a higher refractive index than the effective bulk index of the sensing region, the transmission effect and field shifting effect would partially counteract each other. For aqueous experiments, low refractive index spin-on polymers such as Teflon AF (n=1.31) (Dupont, Wilmington, Del.) can be used for the upper cladding of reference regions to make it a similar refractive index as the water-based sample. It is worthwhile to note that a third sensing mechanism is present in the device. As the refractive index of the sensing region increases, scattering loss, which is proportion to $\Delta n2$ will also decrease, further contributing to a decrease in photocurrent.

5. Experiment and Results 5.1 Photocurrent Measurements

The photocurrent at each detector $I_{det,i}$ is measured at a sampling rate of 4 kHz using the circuit described in Section 3. A probe card was used to probe the chip's metal output pads. Due to the high Schottky barrier produced by the Ti/Si contacts on the chip, measured dark currents were uniformly small (~15 nA), and negligible compared to the measured photocurrent, which was on the order of 1-0.5 µA, depending on detector position. For consistency, the dark current at each detector was subtracted from the measured current, in order to compute the actual photocurrent.

To normalize for fluctuations in coupled light intensity due to source instability and fiber movement, the photocurrent $I_{ref}$ in the $3^{rd}$ detector in the upstream reference region is measured immediately after each detector channel measurement, in order to calculate the normalized photocurrent of $I_{normalized,i}=I_{det,i}/I_{ref}$. Sesame oil, peanut oil, and a 50:50 sesame oil/peanut oil blend were used as fluids for the experiments. Both oils have negligible absorption at 654 nm, as measured by absorption spectrometry. The refractive indices of sesame (n=1.4722), peanut (n=1.4680), and blend (n=1.4702) were measured using an Abbe refractometer.

As the sensing region of the chip is as small as just 0.005 $mm^2$ for a single-analyte, it is conceivable that hundreds or thousands of analytes could be detected on a densely integrated LEAC chip, in an embodiment this is done by providing multiple sensing regions each tagged with a different protein, such as an antibody, having particular sensitivity to a separate analyte. Further, it is anticipated that the core, upper cladding, and lower cladding layers as those terms are used throughout this document may be formed from multiple, thin, sublayers, that those sublayers may include fluid barrier sublayers, so long as the core and cladding layers continue to function as an optical waveguide.

Combinations

An improved analyte-detection system designated A is of the type having an optical waveguide having first and second cladding layers adjacent to a core, the core transparent at a first wavelength; a light source coupled to provide light of the first wavelength to the waveguide; a photodetector having an absorber disposed near the first cladding layer and configured to detect light escaping from the waveguide at the first wavelength; multiple, separate, photocurrent collection lines, where each photocurrent collection line is configured to collect current from a different portion of the photodetector absorber; and at least one amplifier for receiving photocurrent. The analyte detection system is improved because the photodetector absorber is an undivided absorber region for multiple the photocurrent collection lines.

A detection system designated AA includes the detection system designated A wherein the second cladding layer has at least a sensing portion configured to respond to presence of an analyte with a shift of refractive index, the portion configured to respond to an analyte comprising a first portion lying over a portion of the photodetector absorber coupled to a first of the photocurrent collection lines.

A detection system designated AB includes the detection system designated A or AA wherein the second cladding layer has at least a portion configured as a reference section that has lower response to analyte than the sensing portion, the portion configured as a reference section comprising lying over a portion of the photodetector absorber coupled to a second of the photocurrent collection lines.

A detection system designated AC includes the detection system designated A, AA, or AB wherein each amplifier of a plurality of the amplifiers is configured to receive photocurrent from a separate photocurrent collection line of the photocurrent collection lines.

A detection system designated AD including the detection system designated A, or AB wherein at least one amplifier is configured to receive photocurrent from analog multiplexing circuitry, the analog multiplexing circuitry configured to couple a first photocurrent collection line to the at least one current-sensing amplifier and a second photocurrent collection line to a bias line when a control input is in a first state, and the second photocurrent collection line to the at least one current-sensing amplifier and the first photocurrent collection line to the bias line when the control input is in a second state.

An improved analyte-detection system designated B is of the type having an optical waveguide having first and second cladding layers adjacent to a core, the core transparent at a first wavelength; a light source coupled to provide light of the first wavelength to the core of the waveguide; a photodetector selected from the group consisting of metal-semiconductor-metal, vertical PIN, and horizontal PIN photodetectors, the photodetector having an absorber disposed near the first cladding layer and configured to detect light escaping from the waveguide at the first wavelength; multiple, separate, photocurrent collection lines, where each photocurrent collection line is configured to collect current from a separate portion of the photodetector absorber; and at least one current-sensing amplifier for receiving photocurrent. The analyte detection system is improved because the photodetector absorber is an undivided absorber region for multiple photocurrent collection lines. Either separate amplifiers are provided for each of the multiple photocurrent collection lines or multiplexing logic couples selected photocurrent collection line or lines to one or more amplifiers, while coupling each unselected photocurrent collection line to a bias generator, A detection system designated BB including the detection system designated A, AA, AB, AC, AD or B wherein the first wavelength is between 200 and 5000 nanometers.

A detection system designated BC including the detection system designated BB wherein the first wavelength between 400 and 2000 nanometers.

A detection system designated BD including the detection system designated A, AA, AB, AC, AD, B, BB, or BC wherein the photodetector is a metal-semiconductor-metal detector.

A detection system designated BE including the detection system designated A, AA, AB, AC, AD, B, BB, or BC wherein the photodetector is a P-intrinsic-N (PIN) photodiode detector.

A detection system designated BF including the detection system designated A, AA, AB, AC, AD, B, BB, or BC wherein the photodetector is a lateral PIN detector.

A detection system designated BG including the detection system designated A, AA, AB, AC, AD, B, BB, BC, BD, BE, or BF wherein the at least one amplifier is a transimpedance amplifier.

A detection system designated BH including the detection system designated A, AA, AB, AC, AD, B, BB, BC, BD, BE, BF or BG wherein the second cladding layer has a second sensing portion configured to respond to presence of a second analyte, the second sensing portion lying over a portion of photodetector absorber coupled to a third of the photocurrent collection lines.

A detection system designated BJ including the detection system designated A, AA, AB, AC, AD, B, BB, BC, BD, BE, BF, BG, or BH wherein the second cladding layer is present in a reference section lying over a portion of the photodetector absorber coupled to a second of the photocurrent collection lines, and the second cladding layer is absent in a sensing section lying over a first of the photocurrent collection lines.

A method designated C of sensing concentrations of an analyte in a solution includes exposing an first cladding of a waveguide to the solution, the upper cladding being sensitized to the analyte; providing light to a core of the waveguide; sensing leakage through a second cladding of the waveguide with a photodetector having a continuous absorber layer across several distinct portions of the photodetector; collecting current from at least one selected portion of the photodetector; and amplifying the collected current.

A method designated CA including the method designated C further comprising coupling at least one non-selected portion of the photodetector to a bias signal.

While the invention has been particularly shown and described with reference to specific embodiments thereof, it will be understood by those skilled in the art that various other changes in the form and details may be made without departing from the spirit and scope of the invention. It is to be understood that various changes may be made in adapting the invention to different embodiments without departing from the broader inventive concepts disclosed herein and comprehended by the claims that follow.

What is claimed is:

1. An improved detection system of the type comprising:
    an optical waveguide having first and second cladding layers adjacent to a core, the core transparent at a first wavelength;
    a light source coupled to provide light of the first wavelength to the waveguide;
    a photodetector having a photodetector absorber disposed near the first cladding layer, the photodetector absorber configured to detect light of the first wavelength escaping from the waveguide through the first cladding layer;
    a plurality of separate photocurrent collection lines, where each photocurrent collection line is configured to collect current from a different portion of the photodetector absorber; and
    at least one amplifier adapted to receive photocurrent;
    the improvement comprising the photodetector absorber being configured as an undivided photoelectric absorber region for a plurality of the photocurrent collection lines; and
    wherein the detection system is configured such that the light escaping from the waveguide through the first cladding layer is alterable by an analyte applied to the second cladding layer.

2. An improved detection system of the type comprising:
    an optical waveguide having first and second cladding layers adjacent to a core, the core transparent at a first wavelength;
    a light source coupled to provide light of the first wavelength to the waveguide;
    a photodetector having a photodetector absorber disposed near the first cladding layer, the photodetector absorber configured to detect light of the first wavelength escaping from the waveguide through the first cladding layer;
    a plurality of separate photocurrent collection lines, where each photocurrent collection line is configured to collect current from a different portion of the photodetector absorber; and at least one amplifier adapted to receive photocurrent;
the improvement comprising the photodetector absorber being configured as an undivided absorber region for a plurality of the photocurrent collection lines,
and wherein the second cladding layer has at least a sensing portion configured to respond to presence of an analyte with a shift of refractive index, the portion configured to respond to an analyte comprising a first section lying over a portion of the photodetector absorber coupled to a first of the photocurrent collection lines.

3. The detection system of claim 2 wherein the second cladding layer has at least a portion configured as a reference section that has a lower response to presence of the analyte than the sensing portion, the portion configured as a reference section lying over a portion of the photodetector absorber coupled to a second of the photocurrent collection lines.

4. The detection system of claim 2 wherein the second cladding layer has a second sensing portion configured to respond to presence of a second analyte, the second sensing portion lying over a portion of photodetector absorber coupled to a third of the photocurrent collection lines.

5. An improved detection system of the type comprising:
an optical waveguide having first and second cladding layers adjacent to a core, the core transparent at a first wavelength;
a light source coupled to provide light of the first wavelength to the waveguide;
a photodetector having a photodetector absorber disposed near the first cladding layer, the photodetector absorber configured to detect light of the first wavelength escaping from the waveguide through the first cladding layer;
a plurality of separate photocurrent collection lines, where each photocurrent collection line is configured to collect current from a different portion of the photodetector absorber; and
at least one amplifier adapted to receive photocurrent;
the improvement comprising the photodetector absorber being configured as an undivided absorber region for a plurality of the photocurrent collection lines, and
wherein the second cladding layer is present in a reference section lying over a portion of the photodetector absorber coupled to a second of the photocurrent collection lines, and the second cladding layer is absent in a sensing section lying over a first of the photocurrent collection lines.

6. The detection system of claim 1 wherein each current-sensing amplifier of a plurality of the current sensing amplifiers is configured to receive photocurrent from a separate photocurrent collection line of the photocurrent collection lines.

7. An improved detection system of the type comprising:
an optical waveguide having first and second cladding layers adjacent to a core, the core transparent at a first wavelength;
a light source coupled to provide light of the first wavelength to the waveguide;
a photodetector having a photodetector absorber disposed near the first cladding layer, the photodetector absorber configured to detect light of the first wavelength escaping from the waveguide through the first cladding layer;
a plurality of separate photocurrent collection lines, where each photocurrent collection line is configured to collect current from a different portion of the photodetector absorber; and
at least one amplifier adapted to receive photocurrent;
the improvement comprising the photodetector absorber being configured as an undivided absorber region for a plurality of the photocurrent collection lines, and
wherein at least one current-sensing amplifier is configured to receive photocurrent from analog multiplexing circuitry, the analog multiplexing circuitry configured to couple a first photocurrent collection line to the at least one current-sensing amplifier and a second photocurrent collection line to a bias line when a control input is in a first state, and the second photocurrent collection line to the at least one current-sensing amplifier and the first photocurrent collection line to the bias line when the control input is in a second state.

8. The detection system of claim 2, 3, 4, 5, or 7 wherein the first wavelength is between 200 and 5000 nanometers.

9. The detection system of claim 8 wherein the first wavelength is between 400 and 2000 nanometers.

10. The detection system of claim 8 wherein the photodetector is a metal-semiconductor-metal detector.

11. The detection system of claim 8 wherein the photodetector is a P-intrinsic-N (PIN) photodiode detector.

12. The detection system of claim 11 wherein the photodetector is a lateral PIN detector.

13. The detection system of claim 8 wherein the at least one amplifier adapted to receive photocurrent is a transimpedance amplifier.

14. An improved analyte-detection system comprising:
an optical waveguide having first and second cladding layers adjacent to a core, the core transparent at a first wavelength;
a light source coupled to provide light of the first wavelength to the core of the waveguide;
a photodetector selected from the group consisting of metal-semiconductor-metal, vertical PIN, and horizontal PIN photodetectors, the photodetector having an absorber disposed near the first cladding layer and configured to detect light escaping from the waveguide at the first wavelength; multiple, separate, photocurrent collection lines, where each photocurrent collection line is configured to collect current from a separate portion of the photodetector absorber; and at least one current-sensing amplifier for receiving photocurrent;
wherein the photodetector absorber is an undivided absorber region for multiple photocurrent collection lines; and
either separate amplifiers are provided for each of the multiple photocurrent collection lines or multiplexing logic couples N selected photocurrent collection lines to N amplifiers, where N is greater than or equal to one, while coupling each unselected photocurrent collection line to a bias generator.

15. A method of sensing concentrations of an analyte in a solution comprising:
exposing a first cladding of a waveguide to the solution, the first cladding being sensitized to the analyte; providing light to the waveguide;
sensing light leakage through a second cladding of the waveguide with a photodetector having a continuous absorber layer across several distinct portions of the photodetector;
collecting current from at least one selected portion of the photodetector; and amplifying the collected current;
wherein the light provided to the waveguide and the light sensed by the photodetector have the same wavelength.

16. The method of claim 15 further comprising coupling at least one non-selected portion of the photodetector to a bias signal.

17. The method of claim 15 wherein the first cladding comprises the solution.

* * * * *